US00PP21987P3

(12) United States Plant Patent
Danziger

(10) Patent No.: US PP21,987 P3
(45) Date of Patent: Jun. 21, 2011

(54) *LOBELIA* PLANT NAMED 'DANANAB8'

(50) Latin Name: *Lobelia erinus*
Varietal Denomination: DANANAB8

(75) Inventor: Gabriel Danziger, Beit Dagan (IL)

(73) Assignee: Danziger "DANFlower Farm" (IL)

( * ) Notice: Subject to any disclaimer, the term of this patent is extended or adjusted under 35 U.S.C. 154(b) by 0 days.

(21) Appl. No.: 12/454,554

(22) Filed: May 18, 2009

(65) Prior Publication Data

US 2010/0293690 P1 Nov. 18, 2010

(51) Int. Cl.
*A01H 5/00* (2006.01)

(52) U.S. Cl. ..... Plt./451

(58) Field of Classification Search ..... Plt./451
See application file for complete search history.

*Primary Examiner* — June Hwu

(57) ABSTRACT

A new and distinct *Lobelia* cultivar named 'DANANAB8' is disclosed, characterized by having contrasting blue and white flowers, upright plant habit, and early flowering. The new variety is a *Lobelia*, normally produced as an outdoor garden or container plant.

2 Drawing Sheets

Latin name of the genus and species: *Lobelia erinus*.
Variety denomination: 'DANANAB8'.

BACKGROUND OF THE INVENTION

The new *Lobelia* cultivar is a product of a planned breeding program conducted by the inventor, Gabriel Danziger, in Moshav Mishmar Hashiva, Israel. The objective of the breeding program was to produce new varieties of *Lobelia* for commercial introduction. The seed parent is the unpatented, proprietary variety referred to as *Lobelia erinus* 'LOB-6-478.' The pollen parent is the unpatented, proprietary variety referred to as *Lobelia erinus* 'LOB-6241.' The new variety was discovered in April 2006 by the inventor in a group of seedlings resulting from that crossing, in a commercial greenhouse in Moshav Mishmar Hashiva, Israel. Asexual reproduction of the new cultivar 'DANANAB8' by vegetative cuttings was first performed at a commercial greenhouse in Moshav Mishmar Hashiva, Israel in July 2006. Subsequent propagation has shown that the unique features of this cultivar are stable and reproduced true to type on successive generations.

SUMMARY OF THE INVENTION

The cultivar 'DANANAB8' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANANAB8.' These characteristics in combination distinguish 'DANANAB8' as a new and distinct *Lobelia* cultivar:

1. Upright plant habit.
2. Sharp contrasting flower coloration between white and blue.
3. Early blooming compared to similar *Lobelia* cultivars.

PARENTAL COMPARISON

Plants of the new cultivar 'DANANAB8' are similar to plants of the seed parent, 'LOB-6-478' in most horticultural characteristics, however, plants of the new cultivar 'DANANAB8' have a darker color blue flower and more upright plant habit.

Plants of the new cultivar 'DANANAB8' are similar to plants of the pollen parent, 'LOB-6241' in most horticultural characteristics, however, plants of the new cultivar 'DANANAB8' have a different plant habit and different branching characteristics.

COMMERCIAL COMPARISON

Plants of the new cultivar 'DANANAB8' can be compared to the commercial variety 'DANANAB2,' U.S. Plant Pat. No. 19,332. Plants of 'DANANAB8' are similar to plants of 'DANANAB2,' in most horticultural characteristics, however, plants of the new variety have an upright growth habit, compared to the trailing growth habit of 'DANANB2.'

BRIEF DESCRIPTION OF THE PHOTOGRAPH

Figure 1:
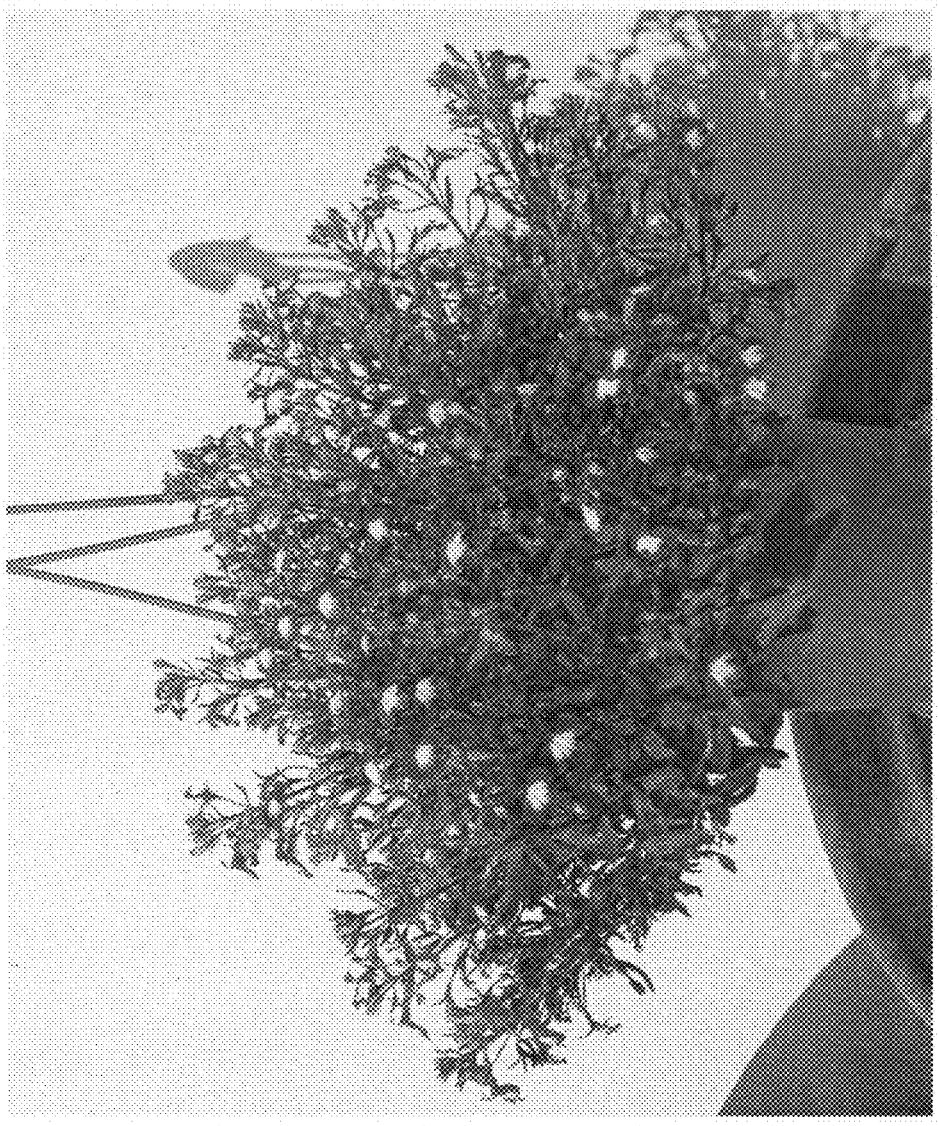

The accompanying photographs in FIG. 1 illustrates in full color a typical plant of 'DANANAB8' grown in a greenhouse, in a 13 cm pot.

Figure 2:
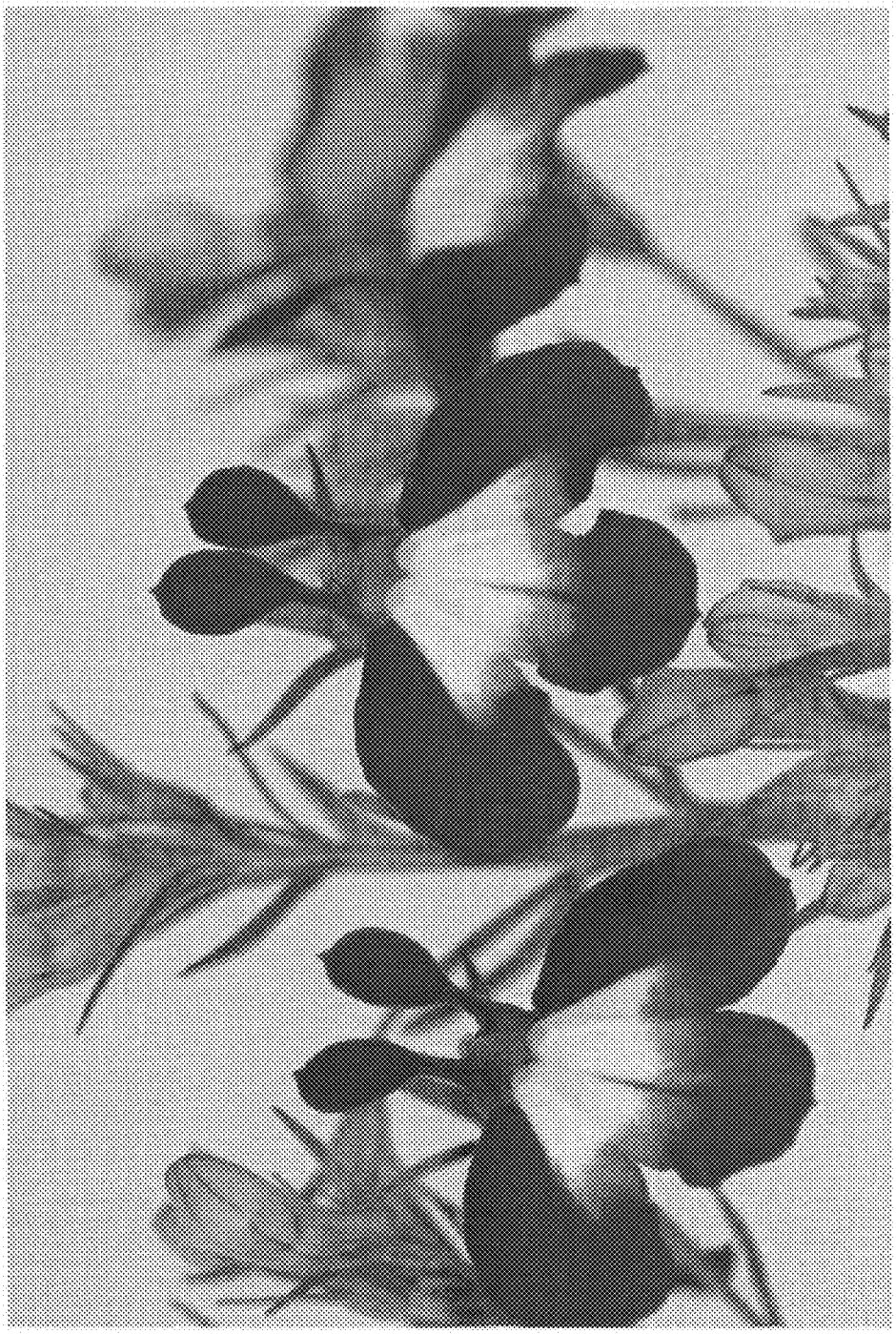

FIG. 2 illustrates in full color a typical flower of 'DANANAB8.'

Age of the plant photographed is approximately 6 weeks from a rooted cutting, with 2 rooted cuttings planted in the pot shown. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANANAB8' plants grown in a greenhouse in Moshav Mishmar Hashiva, Israel. The growing temperature ranged from day temperatures of 18° C. to 25° C., and night temperatures of 12° C. to 18° C. A balanced fertilizer of 75 to 200 ppm Nitrogen was used. Day length of 11-14 hours. The greenhouse is un-shaded, giving bright, normal sunlight conditions. Measurements and numerical values represent averages of typical plant types.

Botanical classification: *Lobelia erinus* cultivar 'DANANAB8.'

PROPAGATION

Time to initiate roots: About 8 to 14 days at approximately 25° C.

Root description: Fibrous.

PLANT

Growth habit: Mounding.

Pot size of plant described: 13 cm.

Height:

*To top of flowers.*—Approximately 20 cm, measured from the soil level of the pot.

Plant spread: Approximately 30 cm.

Growth rate: Very fast.

Branching characteristics: Medium branching.

Length of lateral branches: Approximately 12-17 cm.

Diameter of lateral branches: Approximately 0.2 cm.

Color of branches: Near RHS Green 139 B.

Texture: Pubescent.

Internode length: Approximately 2.0 cm.

Age of plant described: Approximately 50 days from a rooted cutting.

FOLIAGE

Arrangement: Alternate.

Leaves per branch: Approximately 10.

Leaves:

*Size.—Length: About* 1.8 cm. Width: About 0.4 cm. Shape of leaf: Oblanceolate. Shape of apex: Acute. Shape of base: Cuneate. Texture: Glabrous. Aspect: 90° relative to the branch. Margin type: Entire.

*Color.*—Young leaves: Upper surface: Near RHS Green 139 A. Lower surface: Near RHS Green 139 B. Mature leaves: Upper surface: Near RHS Green 139 B. Lower surface: Near RHS Green 139 C.

Petiole: No Petiole.

Veins:

*Venation pattern.*—Pinnate.

*Color.*—Upper surface: Near RHS Green 139 B. Lower surface: Near RHS Green 139 B.

FLOWER

Bud:

*Shape.*—Flattened oval.

*Diameter.*—Approximately 0.3-0.4 cm.

*Length.*—Approximately 0.4 cm.

*Color.*—Near RHS Yellow 1C.

Natural flowering season: Early Spring to Fall in Israel.

Flower type and habit: Bilabiate corolla, individual flowers occurring along axil.

Corolla:

*Upper petals* (*upper lip*).—Number: 2. Length: Approximately 1 cm. Width: Approximately 0.5 cm.

*Shape.*—Elliptic. Aspect: 45 degrees to branch. Margin: entire. Texture: smooth.

*Color.*—When opening: Upper surface: Near RHS Blue 105A. Lower surface: Near RHS Blue 104B. Fully opened: Upper surface: Near RHS Blue 104B. Lower surface: Near RHS Blue 104B.

*Lower petal* (*lower lip*).—Length: 1.5 cm. Width: 0.8 cm. Shape: close to reniform. Apex shape: blunt. Color: Upper surface: Near RHS Blue 105A with White N155A center. Lower surface: Near RHS Blue 105A with White N155A center.

*Palate.*—Length: 8 mm. Width: 5 mm. Color: Near RHS Yellow 4B. Texture: pubescent.

*Throat.*—Outer throat color: Near RHS Blue 105D. Inner Throat Color: Near RHS Blue 104C. Length: 6 mm. Width: 5 mm. Texture: Smooth. Pubescence: none.

Calyx:

*Form.*—Oblanceolate.

*Length.*—Approximately 0.6 cm.

*Diameter.*—Approximately 0.1 cm.

*Sepal.*—Width: 1 mm. Shape: Ligulate. Apex: acute. Margin: Entire. Texture: Smooth. Color: Upper surface: Near RHS Green 139 B. Lower surface: Near RHS Green 139 B.

Pedicel:

*Strength.*—Fragile.

*Aspect.*—Upright.

*Length.*—8 mm.

*Diameter.*—0.5 mm.

*Texture.*—Glabrous.

*Color.*—Near RHS Yellow-Green 144A.

Fragrance. None.

REPRODUCTIVE ORGANS

Stamens:

*Number* (*per flower*).—1.

*Filament length.*—About 1 cm.

*Anthers.*—Shape: Cylindrical. Length: About 0.2 mm. Color: Near RHS Black 202 B.

Pollen:

*Color.*—Near RHS Yellow 11 B.

*Amount.*—Scant.

Pistils:

*Quantity per flower.*—1.

*Length.*—About 1 cm.

*Styles.*—Length: About 0.9 cm. Color: Near RHS Yellow-Green N144 B.

*Stigma.*—Shape: Disc. Color: Near RHS Black 202A with white hair.

OTHER CHARACTERISTICS

Disease resistance: Neither resistance nor susceptibility observed.

Temperature tolerance: The new variety tolerates temperatures between 5 to 35° C.

Seed and fruit production: Produces large amounts of seed.

What is claimed:

1. A new and distinct cultivar of *Lobelia* plant named 'DANANAB8' as herein illustrated and described.

* * * * *